United States Patent
Jerebko et al.

(10) Patent No.: US 10,339,655 B2
(45) Date of Patent: Jul. 2, 2019

(54) AUTOMATED IMAGE EVALUATION IN X-RAY IMAGING

(71) Applicant: SIEMENS HEALTHCARE GMBH, Erlangen (DE)

(72) Inventors: Anna Jerebko, Hausen (DE); Clemens Joerger, Forchheim (DE); Francois Nolte, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/854,974

(22) Filed: Dec. 27, 2017

(65) Prior Publication Data

US 2018/0182102 A1 Jun. 28, 2018

(30) Foreign Application Priority Data

Dec. 27, 2016 (DE) .................. 10 2016 226 230

(51) Int. Cl.
| | |
|---|---|
| *G06K 9/00* | (2006.01) |
| *G06T 7/00* | (2017.01) |
| *G06T 7/11* | (2017.01) |
| *A61B 6/00* | (2006.01) |
| *G06K 9/62* | (2006.01) |

(52) U.S. Cl.
CPC ............. *G06T 7/0014* (2013.01); *A61B 6/54* (2013.01); *G06K 9/6202* (2013.01); *G06T 7/11* (2017.01); *G06T 2207/10116* (2013.01); *G06T 2207/30052* (2013.01); *G06T 2207/30168* (2013.01)

(58) Field of Classification Search
CPC ......... G06T 7/0012; G06T 2207/30168; G06T 7/0014; G06T 1/0007; G06T 2207/10116; G06T 7/11; G06K 9/6201
See application file for complete search history.

(56) References Cited

U.S. PATENT DOCUMENTS

| | | | |
|---|---|---|---|
| 2007/0054350 A1 | 3/2007 | Walker, Jr. | |
| 2013/0190600 A1* | 7/2013 | Gupta | A61B 8/0866 600/410 |
| 2014/0044319 A1* | 2/2014 | Derakhshani | G06K 9/00597 382/117 |
| 2014/0072192 A1 | 3/2014 | Reiner | |

(Continued)

FOREIGN PATENT DOCUMENTS

| | | |
|---|---|---|
| JP | H05130986 A | 5/1993 |
| WO | 2004086941 A2 | 10/2004 |

*Primary Examiner* — Li Liu
(74) *Attorney, Agent, or Firm* — Laurence Greenberg; Werner Stemer; Ralph Locher

(57) ABSTRACT

A method automatically evaluates x-ray image data from an examination region of a patient. X-ray image data is received from the examination region. Furthermore x-ray image data is segmented and anatomical structures are detected in the individual segments. In addition reference image data that comes closest to the segmented x-ray image data is determined. This process is undertaken on the basis of a comparison of the segmented x-ray image data with reference image data from a reference database. The reference image data of the reference database has quality information relating to the image quality of the reference image data in each case. Finally a decision is made on the basis of the quality information of the established reference image data as to whether the received x-ray image data is to be retained or rejected.

13 Claims, 2 Drawing Sheets

(56) References Cited

U.S. PATENT DOCUMENTS

| | | | |
|---|---|---|---|
| 2015/0110348 A1* | 4/2015 | Solanki | G06T 7/0014 |
| | | | 382/103 |
| 2016/0157812 A1* | 6/2016 | Jung | A61B 6/542 |
| | | | 378/16 |
| 2017/0004350 A1* | 1/2017 | Clausen | G06K 9/00087 |
| 2017/0178320 A1 | 6/2017 | Saalbach et al. | |
| 2017/0323587 A1* | 11/2017 | Yagi | G06T 7/11 |
| 2018/0181833 A1* | 6/2018 | Yin | G06T 7/0012 |

* cited by examiner

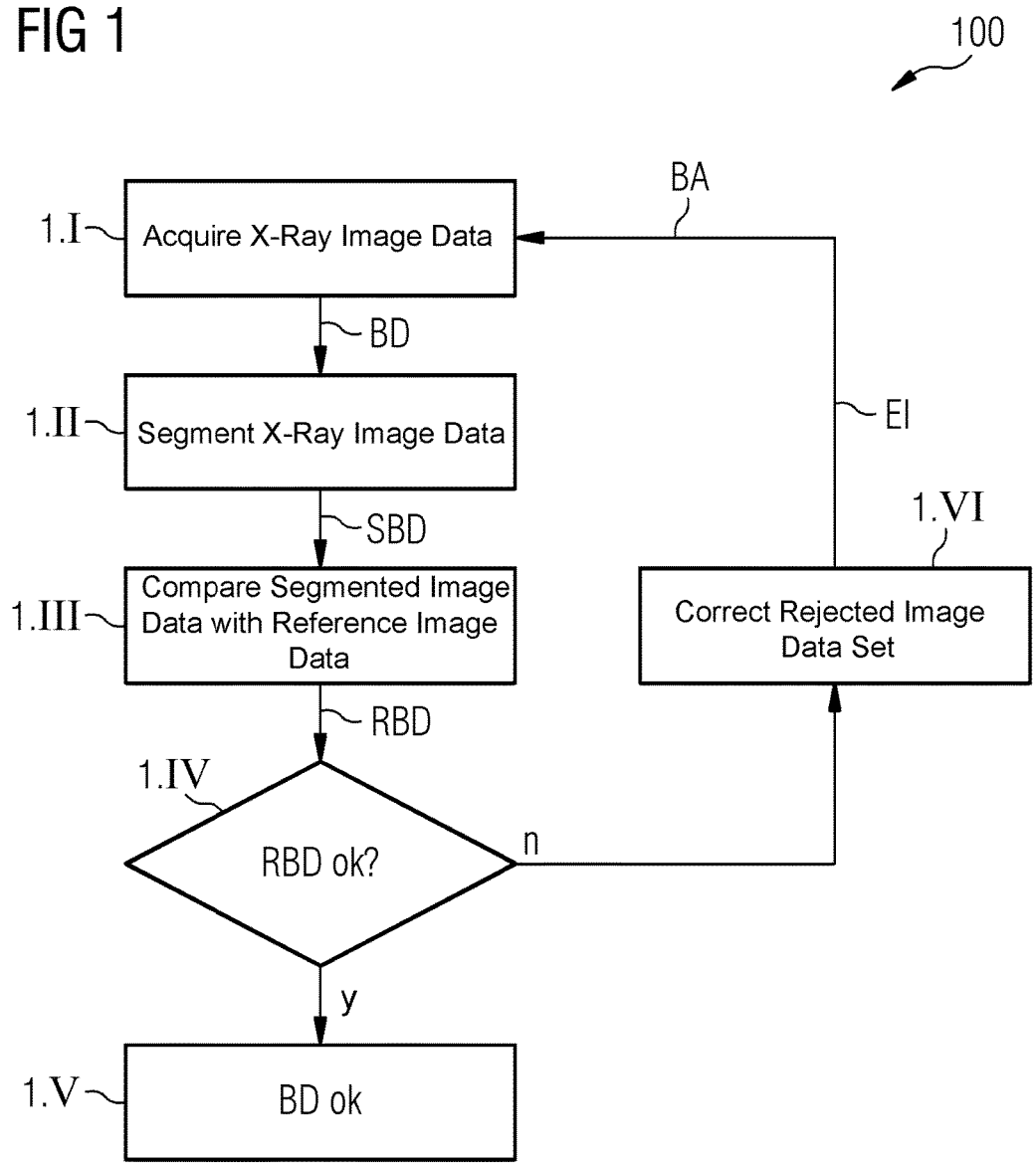

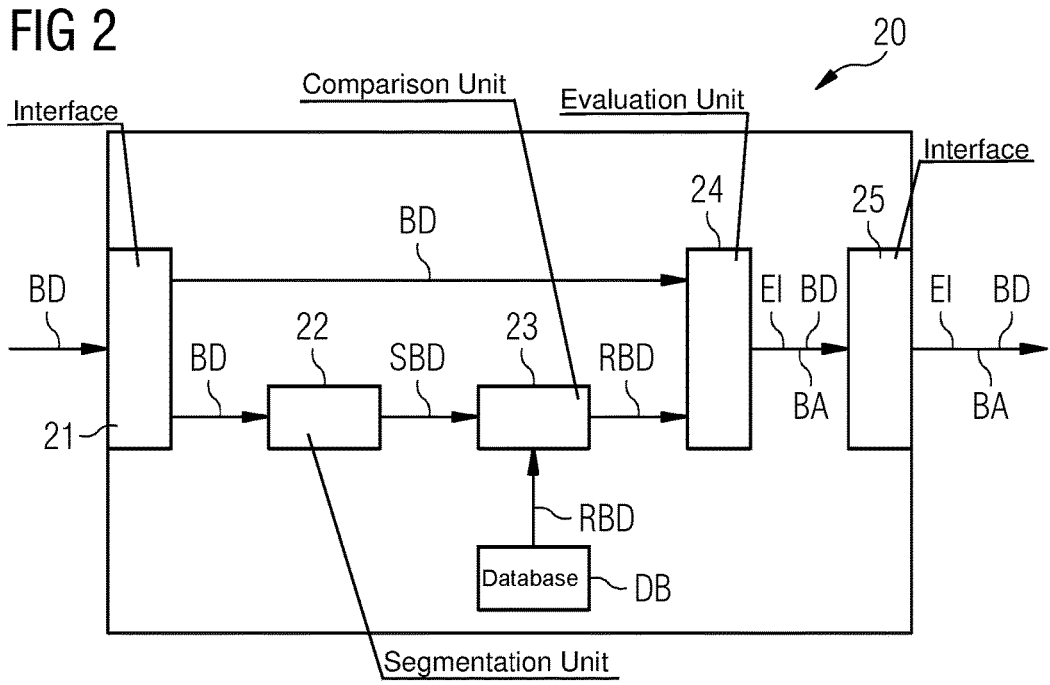
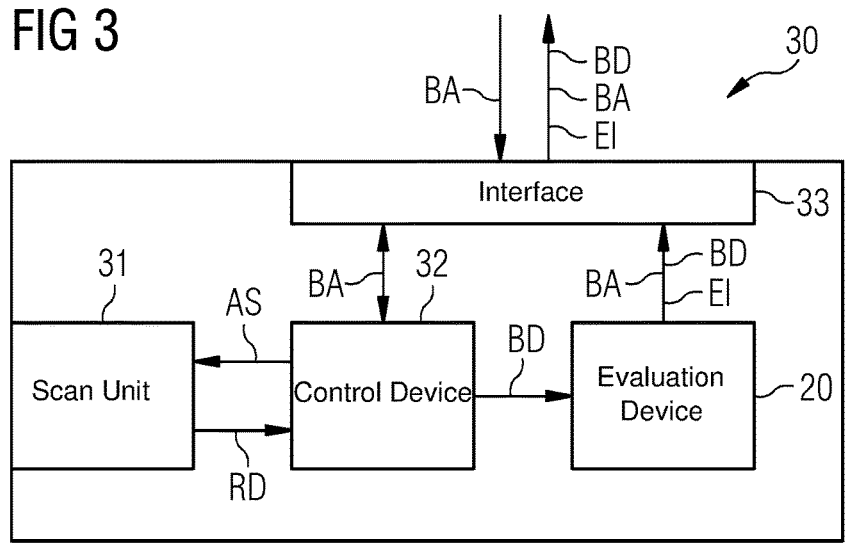

AUTOMATED IMAGE EVALUATION IN X-RAY IMAGING

CROSS-REFERENCE TO RELATED APPLICATION

This application claims the benefit, under 35 U.S.C. § 119, of German patent application DE 10 2016 226 230.0, filed Dec. 27, 2016; the prior application is herewith incorporated by reference in its entirety.

BACKGROUND OF THE INVENTION

Field of the Invention

The invention relates to a method for automated evaluation of x-ray image data. The invention further relates to an imaging method. Moreover the invention relates to an image data evaluation device. In addition the invention relates to an x-ray imaging device.

In digital radiography recorded x-ray images can exhibit quality deficiencies. Such quality deficiencies can be caused by an x-ray radiation dose that is too low, by an x-ray radiation dose that is too high, by a movement of a patient or by an incorrect positioning of a patient. A patient is to be understood in the following as a person to be examined or as an animal to be examined. In such a case it can be necessary to repeat the x-ray radiation therapy and to record an additional image, in order to guarantee that the image shows all clinically relevant parts of the body for a diagnosis. The first image recorded is then no longer used and is removed from the system.

However a renewed exposure of the patient to x-ray radiation is to be avoided, since this is associated with an additional strain on the patient. Over and above this additional time is needed for each patient in the imaging device for each additional recorded image. The decision as to whether a recorded image must be repeated must be made in a very short time during the examination of the patient. Typically the recording of around 1 to 5% of the images must be repeated. The highest level of probability for a repetition occurs with free radiation therapy, with wireless detectors for example.

Previously the images have been evaluated by the x-ray assistant, who sits in a control room to monitor the x-ray imaging system involved while the images are being recorded. The x-ray assistant must evaluate the images under time pressure and must make a decision as to whether the recording of an image must be repeated. Such an evaluation is thus associated with additional time outlay and additional personnel outlay, wherein incorrect classifications of images by the x-ray assistants are also never to be entirely ruled out.

Thus a problem exists in developing a simpler and more time-saving method of evaluating x-ray images.

SUMMARY OF THE INVENTION

This object is achieved by a method for automated evaluation of x-ray image data, by an imaging method, by an image data evaluation and by an x-ray imaging device.

In the inventive method for automated evaluation of x-ray image data from an examination region of a patient x-ray image data is received from the examination region. The x-ray image data can be received directly for example during an imaging process from a reconstruction unit of an x-ray imaging device. The x-ray image data can also originate from an image data memory, in which the x-ray image has been stored after conclusion of an imaging process. Subsequently the x-ray image data is segmented and anatomical structures are detected in the individual segments. The segmentation is preferably carried out on the basis of a machine-learning algorithm, which was trained on a plurality of clinical images, in order to recognize the outlines of organs. In such cases the image segments that are relevant for a later diagnosis will be established. In order to be sure that the right organs have been recognized, there can also be a comparison of the detected anatomical structures with an organ program. Such an organ program has a set of parameters that precisely specifies to an x-ray imaging device how the x-raying is to be carried out. Typically this set is specific for each organ or part of the body (e.g. lower arm, knee, thorax) and is selected by a central x-ray planning system (RIS). On the basis of the parameters of an organ program it can thus be established which anatomical structures are to be acquired with image data to be recorded. The segmented x-ray image data is then compared with reference image data and it is established which of the reference image data comes closest to the segmented x-ray image data. This comparison is carried out automatically with the aid of an image comparison algorithm. The comparison criteria used in such cases can comprise different image parameters and/or information assigned to the images.

To this end the reference image data is read out from a reference database and compared with the relevant image segments. The reference image data of the reference database has quality information in each case relating to the image quality of the reference image data. I.e. the individual datasets of the reference image data are each assigned information which provides details of whether the reference image data was able to be used for a later diagnosis or has been classified as not suitable for this. The reference image data originates from x-ray images recorded earlier and is stored together with the assigned quality information in the reference database. Finally it is decided, on the basis of the quality information of the reference image data established, whether the currently received x-ray image data is suitable for a later diagnosis or must be rejected. In this case the latter means that the x-ray image data is not used for a later diagnosis, but is still stored as reference image data in the reference database, in order to be able to serve as comparison data for later recorded x-ray images. Advantageously x-ray assistants are relieved of the burden of evaluating the image quality during the recorded image. Furthermore, because of the automated comparison, time is saved during imaging. Moreover, because of the automated procedure, errors during the quality assessment because of time pressure, as occur during conventional image evaluation by an x-ray assistant, are avoided. Thus unnecessary repetitions of imaging, which mean an additional dose load for the patient, are avoided.

In the inventive imaging method x-ray projection data is initially acquired from an examination region of a patient with the aid of an x-ray imaging device. This means that x-ray projection images are created with the aid of x-rays from the examination region. Furthermore x-ray image data is created on the basis of the acquired x-ray projection data. This process can for example comprise a reconstruction step and/or one or more image processing processes, for example a filtering process, for image correction. Finally the x-ray image data is evaluated using the inventive method for automated evaluation of x-ray image data from an examination region of a patient and, in the event of its quality being established as sufficient, it is released for image display.

The inventive image data evaluation device has an image data acquisition unit for receiving x-ray image data from an examination region of a patient. Such an image data acquisition unit can have an input interface for receiving x-ray image data for example. The inventive image data evaluation device has a segmentation unit for segmenting the x-ray image data and for detection of anatomical structures in the individual segments. Part of the inventive image data evaluation device is also a comparison unit for establishing reference image data that comes closest to the x-ray image data on the basis of a comparison of the received x-ray image data with reference image data from a reference database. The reference image data of the reference database has quality information in each case relating to the image quality of the reference image data. In addition the inventive image data evaluation device comprises an evaluation unit. The evaluation unit is configured to carry out a decision process, in which it is decided whether the received x-ray image data is qualitatively sufficient or will be rejected. The decision is made on the basis of the quality information of the reference image data established.

The inventive x-ray imaging device has a scan unit for acquisition of x-ray image data from an examination region of a patient, a control device for controlling the scan unit and an inventive image data evaluation device.

The major components of the inventive image data evaluation device can be embodied for the most part in the form of software components. This relates in particular to the segmentation unit, the comparison unit and the evaluation unit. Basically however these components can also be realized in some cases, especially where it is a matter of particularly fast calculations, in the form of software-supported hardware, for example FPGAs or the like. Likewise the interfaces needed, for example when it is only a matter of accepting data from other software components, can be embodied as software interfaces. They can also, however, be embodied as interfaces constructed from hardware for example, which will be activated by suitable software. The image data evaluation device can be part of the x-ray imaging device or can be connected electrically or via a network interface (e.g. DICOM) to such an x-ray imaging device. With the latter variant the potential for upgradability is especially large, since the image data evaluation device, when it is integrated into a network, can be used for evaluating image data from a number of x-ray imaging devices that are connected to the network.

A largely software-based realization has the advantage that even control devices of x-ray imaging devices already in use can be upgraded in a simple manner by a software update, in order to work in the inventive way. In this regard the object is also achieved by a corresponding computer program product with a computer program, which is able to be loaded directly into a memory device of an x-ray imaging device, with program sections for carrying out all steps of the inventive method when the computer program is executed in the x-ray imaging device. As already mentioned, such a computer program, instead of being stored directly in an x-ray imaging device, can also be stored in a computer connected to a data transmission network, which serves to evaluate image data from different imaging devices connected to the data transmission network.

Such a computer program product, as well as the computer program, may possibly comprise additional elements such as e.g. documentation and/or additional components, including hardware components, such as e.g. hardware keys (dongles etc.) for the use of software.

A computer-readable medium, for example a memory stick, a hard disk or any other transportable or permanently installed data medium, on which the program sections of the computer program able to be read in and executed by the processing unit can serve for transport to a storage device of such an x-ray imaging device and/or for storage at the x-ray imaging device or possibly in a computer of the data transmission network. The processor unit can have one or more microprocessors or the like working together for this purpose.

The dependent claims and also the description below each contain especially advantageous embodiments and developments of the invention. In such cases the claims of one claim category in particular can also be further developed analogously to the dependent claims of another claim category or their description parts. In addition the various features of different exemplary embodiments and claims can also be combined, within the framework of the invention, into new exemplary embodiments.

In one embodiment of the inventive method for automated evaluation of x-ray image data from an examination region of a patient, the comparison of the segmented x-ray image data with reference image data is made of the basis of a detected anatomical structure of interest in the segmented x-ray image data. This means that an anatomical structure in the current recorded x-ray image data is compared with a corresponding anatomical structure in the reference image data.

Such a comparison on the basis of a detected anatomical structure of interest in the segmented x-ray image data with the reference image data can be made for example on the basis of at least one of the following criteria:
a) the form of the structure,
b) the size of the structure,
c) the absorption distribution in the structure,
d) the existence of implants in the structure and the type of the implants,
e) the occurrence of fatalities, fractures,
f) the image context,
g) the distribution of the gray levels in the image, and
h) recording parameters.

Combinations of the criteria can also be used to find suitable reference image data. In this way a reference image dataset that comes closest to the current recorded x-ray image can be sought from the reference database. The reliability of the evaluation result is thus increased accordingly.

Preferably, during the inventive method for automated evaluation of x-ray image data, one or more reference image datasets are established from an examination region of a patient during the establishment of closest reference image data and the received x-ray image data is retained when at least one of the reference image datasets has not been rejected, i.e. the quality of at least one of the reference image datasets has been declared to be sufficient. It can occur that a majority of reference image datasets come similarly close to the current image dataset. It is then sufficient for one of the reference image datasets to have been classified as qualitatively sufficient. It can also be the case that, in the case of disease pathologies (e.g. knee with arthrosis versus knee without arthrosis) a number of image datasets deliver different results, although they are similar in terms of x-ray technology. In this case that reference image, which is assigned to the same disease pathology as the image data to be evaluated is selected as the comparison image. In this way the comparability of the selected reference image data is increased and the reliability of an evaluation result is improved.

Especially preferably the comparison is made on the basis of a detected, anatomical structure of interest in the segmented x-ray image data with the reference image data on the basis of clinical patient data. Clinical patient data can contain preliminary recordings, demographic data, further diagnoses or data relating to the medical history. This data can for example be used combined for the comparison as a supplement to the imaging data described further above, which contributes to an improved comparability of the reference image data established.

In a particularly advantageous variant of the inventive method to be applied for automated evaluation of x-ray image data from an examination region of a patient, closest reference image data is established with the aid of an automated comparison method. As already mentioned, for the selection of suitable reference image data, image structure data and also additional clinical patient data can be used. In an automated execution of the comparison savings can be made in the outlay of time and personnel and the selection of the reference image can be undertaken independently of individual preferences of the personnel, whereby the evaluation method can be configured to be more objective.

In a particularly advantageous embodiment of the inventive method for automated evaluation of x-ray image data from an examination region of a patient, the decision as to whether the received x-ray image data is rejected can be made as a function of whether a system setting, i.e. a setting of parameters of an imaging process, has been changed. If for example in an imaging sequence for a recorded image other system parameters, such as for example a changed recording angle, are used, then a change of this size within an imaging sequence can point to this parameter having been inadvertently changed during the recording. In any event the image may possibly not match the other images of the recording sequence and can be sorted out of said sequence.

Within the framework of a preferred variant of the inventive method for automated evaluation of x-ray image data from an examination region of a patient, in the event of it having been decided that the received x-ray image data will be rejected, one of the following items of information is transferred to the user:
a) Information relating to the reasons for the decision,
b) User instructions for changing the positioning of the patient and/or of parts of an x-ray imaging device used for recording the image data, and
c) Statistics data about rejected image data as a warning about the future recording of corresponding x-ray image data.

In addition to the information relating to the quality properties of the x-ray image data currently being recorded, the user thus also receives information that he can use in order to obtain a better result for a repeated recorded image. Thus the imaging process is further accelerated, the dose load on the patient reduced and the recording convenience increased as a result of the shorter duration.

In a specific variant of the inventive imaging method, in the event of it having been decided in the evaluation step that the received x-ray image data will be rejected, one of the following instructions is transferred to the control device of the x-ray imaging device:
a) Instructions for automated image processing of the rejected image, and
b) Instructions for automated correction of the positioning of the patient and/or of parts of the x-ray imaging device.

Advantageously corrections to improve the image quality are thus made in an automated manner, so that the user does not have to intervene. Thus the imaging result is less dependent on the competence of the operating personnel, so that a sufficient image quality is guaranteed, even with poorly trained personnel.

Other features which are considered as characteristic for the invention are set forth in the appended claims.

Although the invention is illustrated and described herein as embodied in an automated image evaluation in x-ray imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a flow diagram, which illustrates a method for automated evaluation of x-ray image data from an examination region of a patient;

FIG. 2 is a block diagram, with which an image data evaluation device is illustrated in accordance with an exemplary embodiment of the invention; and FIG. 3 is a block diagram, with which an x-ray imaging device in accordance with an exemplary embodiment of the invention is presented.

DETAILED DESCRIPTION OF THE INVENTION

Referring now to the figures of the drawings in detail and first, particularly to FIG. 1 thereof, there is shown a flow diagram 100 is shown, with which a method for automated evaluation of x-ray image data BD from an examination region of a patient is illustrated in accordance with an exemplary embodiment of the invention. In step 1.I x-ray image data BD is acquired from an examination region of a patient. The x-ray image data BD can be received for example during an imaging process from an evaluation unit of an x-ray imaging device. The x-ray image data BD can also originate from an image data memory, in which the x-ray image data BD has been stored after conclusion of an imaging process. In step 1.II a segmentation of the received x-ray image data BD is carried out. In this case an x-ray image corresponding to the x-ray image data BD is divided into segments, which are each assigned to individual organs or organ groups, and segmented image data SBD is created. The segmentation is done automatically based on a machine-learning algorithm, which has been trained on a plurality of clinical images, in order to recognize the outlines of organs. Within the framework of the segmentation, in step 1.II, the anatomical structures assigned to individual segments are also established or are produced by the automatically performed segmentation process, in which individual anatomical structures are recognized and segmented.

Subsequently, in step 1.III, a comparison of the x-ray image data BD or of the image data SBD already segmented in step 1.II is made with reference image datasets RBD from a database on the basis of the detected structures. The reference image datasets RBD comprise x-ray image data from older images. In addition the individual reference image datasets RBD are each assigned information relating to the question of whether the image data has been rejected because of quality deficiencies or exhibits a sufficient quality, so that it could be used as the foundation for a later diagnosis. In step 1.III that reference image dataset RBD from the database that comes closest to the established structures is established. In step 1.IV the additional information assigned to the reference image dataset RBD is now evaluated. If this provides information that the reference image dataset RBD is in order, i.e. that the reference image dataset RBD was not rejected, but was classified as suitable for a later diagnosis, this result is transferred to the image dataset BD to be evaluated. If the image dataset BD to be evaluated is thus classified as suitable, which is indicated in FIG. 1 by "y", then the procedure moves to step 1.V and this image dataset BD is stored for a later diagnosis. In the event of it having been established in step 1.IV that the reference image dataset RBD used in the comparison was rejected, which was indicated in FIG. 1 by "n", the procedure moves to step 1.VI. In step 1.VI the image dataset BD to be evaluated is rejected and instructions BA are given for correction of acquisition parameters, in order to obtain improved image data during a repetition of the recorded image. For example the acquisition parameters comprise a changed patient position or a changed position of individual parts of an imaging device used for image recording. Subsequently the procedure returns to step 1.I and an image of the examination region is recorded once again and subsequently the further steps of the method already described are repeated.

In FIG. 2 an image data evaluation device 20 in accordance with an exemplary embodiment of the invention is shown. The image data evaluation device 20 contains an input interface 21, which receives image data BD and transfers it to a segmentation unit 22 and also to an evaluation unit 24. The segmentation unit 22 creates segmented image data SBD, wherein individual image segments are assigned to individual organs or organ groups. In the segmentation an image region of the image data BD is marked, which corresponds to a region relevant for a later diagnosis. This region can comprise a specific organ or part of the body for example or can comprise a specific organ group, which is to be thoroughly examined during a later diagnosis. This segmented region SBD is then compared by a comparison unit 23 with a plurality of reference image datasets RBD, which are stored in a database DB. The reference image RBD, which contains an image segment that comes closest to the segmented region SBD, is sought and transferred to an evaluation unit 24.

The evaluation unit 24 reads out the quality information assigned to the reference image RBD established and, on this basis, decides whether the image data BD currently being acquired is to be rejected or not. Corresponding result information EI is output via an output interface 25 to a user and/or a control device of an imaging device (see FIG. 3). In the event of a positive result, i.e. in the event that the image BD to be evaluated fulfils predetermined image quality requirements, i.e. was not rejected by the evaluation unit 24, the image data BD currently being acquired is likewise output via the output interface 25. In the event of the evaluation result being negative, i.e. in the event of the image BD to be evaluated not fulfilling predetermined image quality requirements and thus being rejected by the evaluation unit 24, instead of the image data BD currently being recorded, instructions BA are output via the output interface 25, with the aid of which a correction of the acquisition parameters of the imaging acquisition can be undertaken and thus the image recording can be repeated.

In FIG. 3 an x-ray imaging device 30 in accordance with an exemplary embodiment of the invention is shown. Such an x-ray imaging device can be embodied as a computed tomography device for example. The x-ray imaging device 30 contains a scan unit 31 for acquisition of x-ray image data BD from an examination region of a patient. Furthermore a control device 32, with which activation commands AS can be transferred to the scan unit 31 and x-ray projection measurement data RD received and processed into image data BD, is also part of the x-ray imaging device 30. The image data BD is transferred to an image data evaluation device 20, which evaluates the image data BD in the way described in conjunction with FIG. 1 and FIG. 2 and outputs corresponding result information EI and if necessary image data BD or correction instructions BA via a user interface 33. The correction instructions BA can be used to activate the scan unit 31 with changed acquisition parameters AS and in this way can be used to achieve an improved image recording.

In conclusion it is pointed out once again that the method and devices described above merely involve preferred exemplary embodiments of the invention and that the invention can be varied by the person skilled in the art, without departing from the area of the invention, provided it is predetermined by the claims. It is also pointed out for the sake of completeness that the use of the indefinite article "a" or "an" does not exclude the features involved also being able to be present more than once. Likewise the term "unit" does not exclude said unit consisting of a number of components, which can possibly also be physically distributed.

The following is a summary list of reference numerals and the corresponding structure used in the above description of the invention:
AS Control commands
BA User instructions
BD X-ray image data
DB Database
EI Result information
RBD Reference image datasets
RD X-ray projection data
SBD Segmented image data
20 Image data evaluation device
21 Input interface
22 Segmentation unit
23 Comparison unit
24 Evaluation unit
25 Output interface
30 X-ray imaging device
31 Scan unit
32 Control device
33 User interface

The invention claimed is:

1. A method for automated evaluation of x-ray image data from an examination region of a patient, which comprises the steps of:
receiving the x-ray image data from the examination region;
segmenting the x-ray image data resulting in segmented x-ray image data, the x-ray image data being segmented based on anatomical structures detected in individual segments of the x-ray image data;
determining reference image data coming closest to the segmented x-ray image data on a basis of a comparison of the segmented x-ray image data with the reference image data from a reference database, wherein the reference image data of the reference database having quality information relating to image quality of the reference image data; and deciding whether the x-ray image data will be retained or rejected, based on the quality information of the reference image data determined.

2. The method according to claim 1, wherein a comparison of the segmented x-ray image data with the reference image data is made on a basis of a detected anatomical structure of interest in the segmented x-ray image data.

3. The method according to claim 2, wherein the comparison is made on the basis of the detected anatomical structure of interest in the segmented x-ray image data with the reference image data on a basis of at least one of the following criteria:
   form of the detected anatomical structure;
   size of the detected anatomical structure;
   absorption distribution in the detected anatomical structure;
   existence of implants in the detected anatomical structure and type of the implants;
   occurrence of fatalities and fractures;
   image context;
   distribution of gray levels in an image; and
   recording parameters.

4. The method according to claim 2, wherein the comparison is made on a basis of the detected anatomical structure of interest in the segmented x-ray image data with the reference image data on a basis of clinical patient data.

5. The method according to claim 1, wherein when determining a closest reference image data, at least one reference image dataset is determined and the x-ray image data will not be rejected, when at least one of the reference image datasets has not been rejected.

6. The method according to claim 5, wherein the closest reference image data is determined with an aid of an automated comparison method.

7. The method according to claim 1, wherein a decision as to whether the x-ray image data received will be rejected is made on a basis of whether a system setting has been changed.

8. The method according to claim 1, wherein, in an event of it having been decided that the x-ray image data received will be rejected, one of the following items of information will be transferred to a user:
   information relating to reasons for a decision;
   user instructions for changing positioning of the patient and/or of parts of an x-ray imaging device used for recording the x-ray image data; and
   statistical data about rejected image data as a warning about a future recording of corresponding x-ray image data.

9. An imaging method, which comprises the steps of:
   acquiring x-ray projection data from an examination region of a patient with an aid of an x-ray imaging device;
   creating x-ray image data on a basis of the x-ray projection data acquired;
   evaluating the x-ray image data using a method according to claim 1; and
   releasing the x-ray image data for image display in an event a quality of the x-ray image data having been determined as adequate.

10. The method according to claim 9, wherein, in an event of it having been decided in the evaluating step that the x-ray image data received will be rejected, one of the following instructions will be transferred to a control device of the x-ray imaging device:
   instructions for automated image processing of a rejected image; and
   instructions for automated correction of a positioning of the patient and/or of parts of the x-ray imaging device.

11. An image data evaluation system, comprising:
   an image data acquisition interface unit for receiving x-ray image data from an examination region of a patient;
   a segmentation unit for segmentation of the x-ray image data, the x-ray image data being segmented based on detected anatomical structures in individual segments;
   a comparator for determining reference image data coming closest to the x-ray image data on a basis of a comparison of a segmented x-ray image data with the reference image data from a reference database, wherein the reference image data of the reference database has quality information relating to an image quality of the reference image data;
   an evaluator for deciding whether the x-ray image data received will be rejected, on a basis of the quality information of a determined reference image data.

12. An x-ray imaging device, comprising:
   a scanner for acquiring x-ray image data from an examination region of a patient;
   a controller for controlling said scanner; and
   an image data evaluation system according to claim 11.

13. A non-transitory computer-readable medium storing computer executable instructions able to be executed by a processing unit, the computer executable instructions performing a method of automated evaluation of x-ray image data from an examination region of a patient, which comprises the steps of:
   receiving x-ray image data from the examination region;
   segmenting the x-ray image data resulting in segmented x-ray image data, the x-ray image data being segmented based on anatomical structures detected in individual segments of the x-ray image data;
   determining reference image data coming closest to the segmented x-ray image data on a basis of a comparison of the segmented x-ray image data with the reference image data from a reference database, wherein the reference image data of the reference database has quality information relating to image quality of the reference image data; and
   deciding whether the x-ray image data will be retained or rejected, based on the quality information of the reference image data determined.

* * * * *